United States Patent [19]

Flaugh

[11] Patent Number: 4,997,845

[45] Date of Patent: Mar. 5, 1991

[54] BETA-ALKYLMELATONINS AS OVULATION INHIBITORS

[75] Inventor: Michael E. Flaugh, Indianapolis, Ind.

[73] Assignee: Eli Lilly and Company, Indianapolis, Ind.

[21] Appl. No.: 522,408

[22] Filed: May 10, 1990

Related U.S. Application Data

[60] Continuation of Ser. No. 247,056, Sep. 20, 1988, abandoned, which is a division of Ser. No. 10,259, Feb. 2, 1987, abandoned.

[51] Int. Cl.$^5$ .................. A61K 31/40; C07D 209/42; C07D 209/20; C07D 405/06
[52] U.S. Cl. .................................. 514/415; 548/467; 548/492; 548/494; 548/502; 548/503; 548/507
[58] Field of Search .................. 548/507; 514/415

[56] References Cited

U.S. PATENT DOCUMENTS

| | | | |
|---|---|---|---|
| 3,211,744 | 10/1965 | Hofmann et al. | 260/319 |
| 4,087,444 | 5/1978 | Flaugh et al. | 260/326.13 R |
| 4,614,807 | 9/1986 | Flaugh | 548/507 |

FOREIGN PATENT DOCUMENTS 910991 11/1962 United Kingdom .
910992 11/1962 United Kingdom .

OTHER PUBLICATIONS

Pasini, Chem Abs 60, 14601c (1964).
*The Merck Index,* (Tenth Edition 1983) 5633.
Chu et al., *Endocrinology,* 75, 238 (1964).
Ying et al., *Endocrinology,* 92, 333 (1973).
*Chemical Abstracts,* 63, 18192a (1965).
Frohn et al., *Life Sci.,* 27, 2043 (1980).
Flaugh et al., *J. Med. Chem.,* 22, 63 (1979) (Flagh III).
Farlow et al., *Org. Prep. and Proc. Int.,* 13(1), 39 (1981).
Misztal Chemical Abstracts, 92, 128645f (1980).

*Primary Examiner*—Mark L. Berch
*Attorney, Agent, or Firm*—Douglas J. Taylor; Leroy Whitaker

[57] ABSTRACT

β-Alkylmelatonins are useful as ovulation inhibitors.

8 Claims, No Drawings

BETA-ALKYLMELATONINS AS OVULATION INHIBITORS

This application is a continuation of application Ser. No. 247,056 filed Sept. 20, 1988, which is a division of of application Ser. No. 010,259, filed Feb. 2, 1987, both now abandoned.

BACKGROUND OF THE INVENTION

Melatonin, represented by the structure below

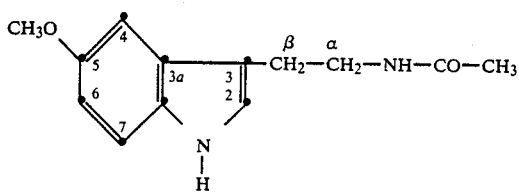

is named systematically as N-[2-(5-methoxy-3-indolyl)ethyl]acetamide. Trivial names for the compound include N-acetyl-5-methoxytryptamine and N-acetyl-O-methylserotonin. Melatonin, a pineal gland hormone, has ovulation inhibitory activity. Chu, Wortman and Axelrod, *Endocrinology*, 75, 238 (1964) inhibited both the estrous phase of the estrous cycle and ovulation in rats and mice with melatonin—see also Ying and Greep, *Endocrinology*, 92, 333 (1973).

Several substituted melatonins have been prepared Flaugh et al, *J. Med. Chem.*, 22, 63 (1979) prepared 6-chloro and 6-fluoromelatonin. These compounds showed increased ovulation blocking activity α-Methyl-6-chloromelatonin was also prepared, but α-methyl substitution was found to have no increased ovulation-blocking activity when compared to melatonin itself.

Frohn et al. *Life Sci.* 27, 2043 (1980) prepared N-acetyl 5,6-dimethoxytryptamine and longer alkyl chain N-acyl derivatives. Frohn et al. discuss structure-activity relationships of melatonin analogs, and conclude that only exchange of acetyl for propionyl or butyryl and halogenation at the 6-position are beneficial. All other changes are said to decrease activity. α-Methyl-6-chloromelatonin was stated to be inactive.

Beta-alkylmelatonins are not described in the prior art. In view of Frohn's teaching that α-methylation destroys activity β-alkylation would not be expected to produce active ovulation inhibitors. An object of this invention is to provide a group of β-alkyl melatonins having good ovulation inhibition activity.

SUMMARY OF THE INVENTION

This invention provides compounds of the formula

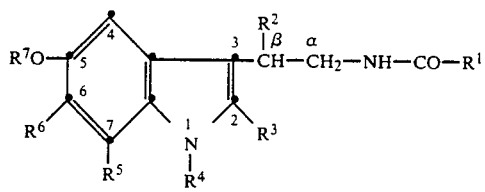

wherein
$R^1$ is H, $C_1$-$C_4$ alkyl, or $C_1$-$C_4$ alkoxy;
$R^2$ is $C_1$-$C_4$ alkyl;
$R^3$ is H;
$R^4$ is H, haloacetyl, $C_1$-$C_5$ alkanoyl, benzoyl, or benzoyl substituted with halo or methyl;
$R^5$ and $R^6$ are individually H or halo; and
$R^7$ is H or $C_1$-$C_4$ alkyl.

The invention also provides pharmaceutical formulations comprising a compound of the above formula together with a pharmaceutically acceptable carrier or diluent, as well as a method for inhibiting ovulation in a female mammal or bird comprising administering an anti-ovulant of the type of beta-alkyl melatonin defined above.

Also contemplated within the scope of this invention are intermediates of the formula

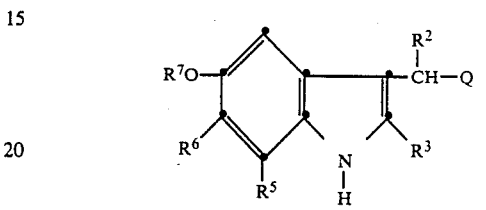

wherein $R^2$, $R^5$, $R^6$, and $R^7$ are as defined above; $R^3$ is H or COOH; and Q is

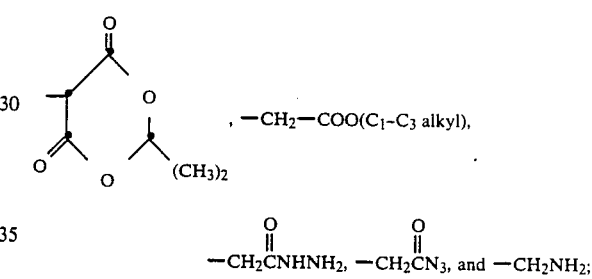

with the provision that when $R^3$ is COOH Q must be —$CH_2NH_2$.

Preferred compounds of the invention are those in which $R^1$ is $C_1$-$C_4$ alkyl, $R^2$ is $C_1$-$C_4$ alkyl, $R^3$ and $R^4$ are H, $R^5$ and $R^6$ are individually H or halo, and $R^7$ is $C_1$-$C_4$ alkyl. Especially preferred compounds are those in which $R^1$, $R^3$, and $R^4$ are as defined for the preferred compounds and $R^2$ is methyl or ethyl, $R^5$ and $R^6$ are individually H, F, or Cl, and $R^7$ is methyl. The most preferred compounds encompassed within this invention are β-methyl-6,7-dichloromelatonin, β-methyl-6-chloromelatonin, and β-methylmelatonin.

DETAILED DESCRIPTION OF THE INVENTION

The following definitions refer to the various terms used above and throughout the disclosure.

The term "halo" refers to fluoro, chloro, bromo, and iodo.

The term "$C_1$-$C_4$ alkyl" refers to the straight and branched aliphatic radicals of 1-4 carbon atoms including methyl, ethyl, propyl, isopropyl, n-butyl, isobutyl, sec-butyl, and tert-butyl.

The term "$C_1$-$C_4$ alkoxy" includes the straight and branched aliphatic ether radicals of 1-4 carbon atoms such as methoxy, ethoxy, propoxy, isopropoxy, n-butoxy, isobutoxy, sec-butoxy, and tert-butoxy.

The term "haloacetyl" refers to chloroacetyl, bromoacetyl, fluoroacetyl, and iodoacetyl.

The term "$C_1$-$C_5$ alkanoyl" includes formyl, acetyl, propionyl, butyryl, α-methylpropionyl, valeryl, α- methylbutyryl, β-methylbutyryl, and pivaloyl. Preferred $C_1$–$C_5$ alkanoyl groups are acetyl and pivaloyl, and most preferably, acetyl.

The term "benzoyl substituted with halo" defines mono- and di-halo benzoyl groups. Specific mono-halo benzoyl groups are chlorobenzoyl, bromobenzoyl, fluorobenzoyl, and iodobenzoyl. Preferably, the monohalo benzoyl group is a 4-halo benzoyl, and the preferred halo substituent is chloro.

The di-halo benzoyl groups included generally are those in which both halo substituents are the same, and, preferably, are those in which the halo substituents are located in the 2- and 4-positions. Typical di-halo benzoyl groups include 2,4-dichlorobenzoyl, 2,4-dibromobenzoyl, 2,4-difluorobenzoyl, and 2,4-diiodobenzoyl. The preferred group is 2,4-dichlorobenzoyl.

The term "benzoyl substituted with methyl" contemplates methylbenzoyl, dimethylbenzoyl, and trimethylbenzoyl. Preferred groups are 2-methylbenzoyl, 2,6-dimethylbenzoyl, 2,4,6-trimethylbenzoyl, and the like.

Illustrative compounds falling within the scope of this invention are:

N-[2-methyl-2-(5-methoxy-6-chloroindol-3-yl)ethyl]acetamide
N-[2-methyl-2-(5-methoxy-6-fluoroindol-3-yl)ethyl]acetamide
N-[2-ethyl-2-(5-methoxy-6-fluoroindol-3-yl)ethyl]acetamide
N-[2-ethyl-2-(5-methoxy-6-chloroindol-3-yl)ethyl]acetamide
N-[2-isopropyl-2-(5-methoxy-6-chloroindol-3-yl)ethyl]acetamide
N-[2-isopropyl-2-(5-methoxy-6-fluoroindol-3-yl)ethyl]acetamide
N-[2-methyl-2-(5-methoxy-6-bromoindol-3-yl)ethyl]formamide
N-[2-butyl-2-(5-methoxy-6-bromoindol-3-yl)ethyl]formamide
N-[2-ethyl-2-(5-propoxy-6-chloroindol-3-yl)ethyl]formamide
N-[2-propyl-2-(5-isopropoxy-6-iodoindol-3-yl)ethyl]formamide
N-[2-methyl-2-(5-methoxy-6-chloroindol-3-yl)ethyl]propionamide
N-[2-ethyl-2-(5-methoxy-6-fluoroindol-3-yl)ethyl]propionamide
N-[2-methyl-2-(5-ethoxy-6-bromoindol-3-yl)ethyl]propionamide
N-[2-methyl-2-(5-ethoxy-6-fluoroindol-3-yl)ethyl]butyramide
N-[2-propyl-2-(5-butoxy-6-chloroindol-3-yl)ethyl]butyramide
N-[2-methyl-2-(5-methoxy-6-chloroindol-3-yl)ethyl]butyramide
N-[2-methyl-2-(5-methoxy-7-chloroindol-3-yl)ethyl]acetamide
N-[2-methyl-2-(5-methoxy-7fluoroindol-3-yl)ethyl]acetamide
N-[2-ethyl-2-(5-methoxy-7chloroindol-3-yl)ethyl]acetamide
N-[2-propyl-2-(5-methoxy-7-bromoindol-3-yl)ethyl]acetamide
N-[2-ethyl-2-(5-t-butoxy-7-chloroindol-3-yl)ethyl]formamide
N-[2-ethyl-2-(5-ethoxy-7-iodoindol-3-yl)ethyl]formamide
N-[2-methyl-2-(5-isopropoxy-7-chloroindol-3-yl)ethyl]formamide
N-[2-methyl-2-(5-methoxy-7-bromoindol-3-yl)ethyl]propionamide
N-[2-ethyl-2-(5-propoxy-7-chloroindol-3-yl)ethyl]propionamide
N-[2-methyl-2-(5-s-butoxy-7-fluoroindol-3-yl)ethyl]propionamide
N-[2-methyl-2-(5-methoxy-7-chloroindol-3-yl)ethyl]butyramide
N-[2-butyl-2-(5-ethoxy-7-chloroindol-3-yl)ethyl]butyramide
N-[2-ethyl-2-(5-methoxy-7-fluoroindol-3-yl)ethyl]butyramide
N-[2-methyl-2-(5-methoxy-6,7-dichloroindol-3-yl)ethyl]acetamide
N-[2-ethyl-2-(5-methoxy-6,7-dichloroindol-3-yl)ethyl]acetamide
N-[2-isopropyl-2-(5-methoxy-6,7-dichloro-indol-3-yl)ethyl]acetamide
N-[2-methyl-2-(5-isopropxy-6,7-dichloro-3-yl)ethyl]acetamide
N-[2-methyl-2-(5-methoxy-6,7-difluoroindol-3-yl)ethyl]acetamide
N-[2-propyl-2-(5-methoxy-6,7-difluoroindol-3-yl)ethyl]acetamide
N-[2-ethyl-2-(5-butoxy-6,7-difluoroindol-3-yl)ethyl]acetamide
N-[2-methyl-2-(5-methoxy-6-chloro-7-fluoro-indol-3-yl)ethyl]acetamide
N-[2-methyl-2-(5-methoxy-6-chloro-7-bromoindol-3-yl)ethyl]acetamide
N-[2-methyl-2-(5-methoxy-6-fluoro-7-chloro-3-yl)ethyl]acetamide
N-[2-methyl-2-(5-ethoxy-6-bromo-7-iodoindol-3-yl)ethyl]acetamide
N-[2-ethyl-2-(5-ethoxy-6-chloro-7-fluoroindol-3-yl)ethyl]acetamide
N-[2-isopropyl)-2-(5-t-butoxy-6-chloro-7-fluoro-indol-3-yl)ethyl]acetamide
N-[2-ethyl-2-(5-butoxy-6-bromo-7-chloroindol-3-yl)ethyl]acetamide
N-[2-methyl-2-(5-methoxy-6,7-dichloroindol-3-yl)ethyl]formamide
N-[2-methyl-2-(5-methoxy-6,7-dibromoindol-3-yl)ethyl]formamide
N-[2-t-butyl-2-(5-methoxy-6-chloro-7-fluoro-indol-3-yl)ethyl]formamide
N-[2-ethyl-2-(5-ethoxy-6-fluoro-7-bromoindol-3-yl)ethyl]formamide
N-[2-ethyl-2-(5-s-butoxy-6-fluoro-7-chloroindole-3-yl)ethyl]formamide
N-[2-methyl-2-(5-methoxy-6,7-dichloroindole-3-yl)ethyl]propionamide
N-[2-ethyl-2-(5-methoxy-6,7-dichloroindol-3-yl)ethyl]propionamide
N-[2-propyl-2-(5-isopropoxy-6-chloro-7-fluoroindol-3-yl)ethyl]propionamide
N-[2-methyl-2-(5-methoxy-6-bromo-7-iodoindol-3-yl)ethyl]propionamide
N-[2-methyl-2-(5-ethoxy-6-bromo-7-chloroindol-3-yl)ethyl]propionamide
N-[2-methyl-2-(5-methoxy-6,7-difluoroindol-3-yl)ethyl]butyramide
N-[2-ethyl-2-(5-methoxy-6-fluoro-7-chloroindol-3-yl)ethyl]butyramide
N-[2-isopropyl-2-(5-methoxy-6,7-dibromoindol-3-yl)ethyl]butyramide
N-[2-isopropyl-2-(5-butoxy-6-bromo-7-chloroindol-3-yl)ethyl]butyramide N-[2-ethyl-2-(5-methoxy-6,7-dichloro-3-yl)ethyl]-butyramide
N-[2-methyl-2-(1-acetyl-5-methoxy-6-chloroindol-3-yl)ethyl]acetamide
N-[2-butyl-2-(1-acetyl-5-methoxy-6-fluoroindol-3-yl)ethyl]acetamide
N-[2-ethyl-2-(1-acetyl-5-isopropoxy-6-chloro-7-fluoroindol-3-yl)ethyl]acetamide
N-[2-methyl-2-(1-propionyl-5-methoxy-6-fluoroindol-3-yl)ethyl]acetamide
N-[2-methyl-2-(1-propionyl-5-ethoxy-6 7-dichloroindol-3-yl)ethyl]acetamide
N-[2-ethyl-2-(1-propionyl-5-butoxy-7-chloroindol-3-yl)ethyl]acetamide
N-[2-methyl-2-(1-pivaloyl-5-ethoxy-6-bromoindol-3-yl)ethyl]formamide
N-[2-propyl-2-(1-chloroacetyl-5-methoxy-6-bromo-7-fluoroindol-3-yl)ethyl]propionamide
N-[2-methyl-2-(1-bromoacetyl-5-ethoxy-7-chloroindol-3-yl)ethyl]butyramide
N-[2-ethyl-2-(1-valeryl-5-isopropoxy-6,7-dichloroindol-3-yl)ethyl]acetamide
N-[2-methyl-2-(1-butyryl-5-methoxy-6-chloroindol-3-yl)ethyl]acetamide
N-[2-ethyl-2-(1-benzoyl-5-t-butoxy-7-bromoindol-3-yl)ethyl]formamide
N-[[2-isopropyl-2-[1-(4-chlorobenzoyl)-5-methoxy-7-fluoroindol-3-yl]ethyl]]formamide
N-[[2-methyl-2-[1-(4-bromobenzoyl)-5-ethoxy-6,7-dichloroindol-3-yl]ethyl]]propionamide
N-[[2-ethyl-2-[1-(2,4-dichlorobenzoyl)-5-methoxy-7-bromoindol-3-yl]ethyl]]propionamide
N-[[2-methyl-2-[1-(2,4-difluorobenzoyl)-5-propoxy-6-chloroindol-3-yl]ethyl]]formamide
N-[[2-methyl-2-[1-(4-iodobenzoyl)-5-ethoxy-6-fluoro-7-chloroindol-3-yl]ethyl]]acetamide
N-[[2-ethyl-2-[1-(2-methylbenzoyl)-5-methoxyindol-3-yl]ethyl]]propionamide
N-[[2-methyl-2-[1-(4-fluorobenzoyl)-5-ethoxyindol-3-yl]ethyl]]formamide
N-[[2-methyl-2-(1-(2,6-dimethylbenzoyl)-5-methoxy-7-fluoroindol-3-yl]ethyl]]formamide
N-[[2-ethyl-2-[1-(2,6-dimethylbenzoyl)-5-ethoxyindol-3-yl]ethyl]]acetamide
N-[[2-ethyl-2-[1-(2,4,6-trimethoxybenzoyl)-5-methoxy-6-chloroindol-3-yl]ethyl]]propionamide
N-[[2-methyl-2-[1-(2,4,6-trimethoxybenzoyl)-5-methoxyindol-3-yl]ethyl]]formamide
N-[2-ethyl-2-(1-pivaloyl-5-isopropoxyindol-3-yl)ethyl]acetamide
N-[2-methyl-2-(1-chloroacetyl-5-methoxyindol-3-yl)ethyl]butyramide
N-[2-methyl-2-(5-methoxyindol-3-yl)ethyl]acetamide
N-[2-ethyl-2-(5-methoxyindol-3-yl)ethyl]acetamide
N-[2-ethyl-2-(5-methoxyindol-3-yl)ethyl]propionamide
N-[2-methyl-2-(5-propoxyindol-3-yl)ethyl]formamide
N-[2-methyl-2-(5-s-butoxyindol-3-yl)ethyl]butyramide
N-[2-ethyl-2-(5-ethoxyindol-3-yl)ethyl]propionamide
N-[2-methyl-2-(5-ethoxyindol-3-yl)ethyl]formamide
N-[2-isopropyl-2-(5-methoxyindol-3-yl)ethyl]acetamide
N-[2-ethyl-2-(5-methoxyindol-3-yl)ethyl]formamide;
and the like.

The compounds of this invention may be prepared according to any of several processes employing common reactants and procedures. A typical process for preparing the invention compounds comprises acylating a β-alkyl tryptamine. The β-alkyl tryptamines are prepared from indoles. The overall scheme is shown below.

Reaction Scheme I

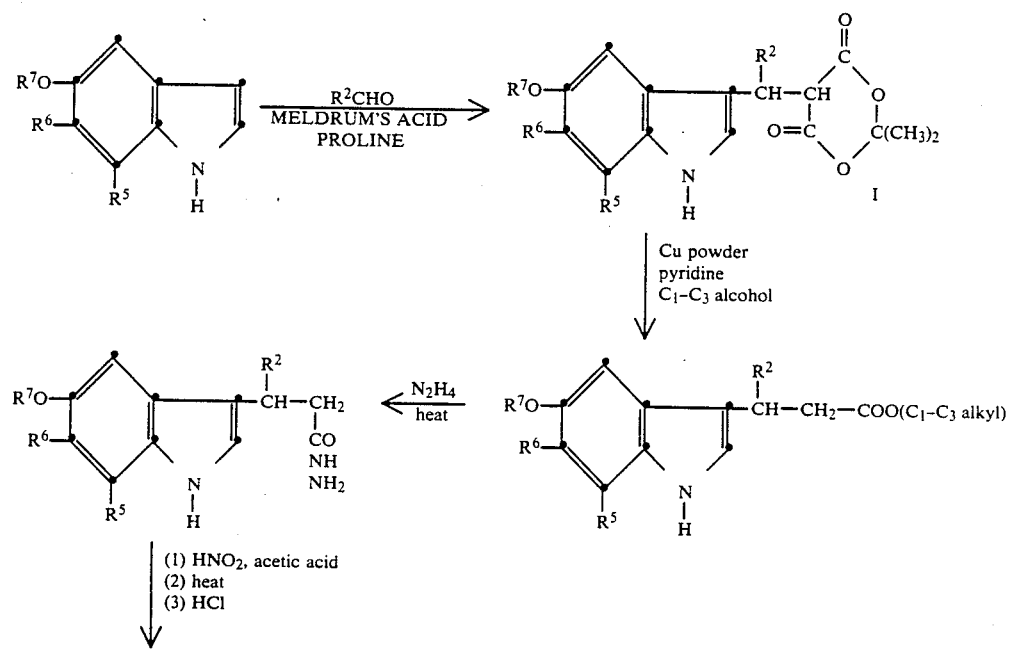

-continued
Reaction Scheme I

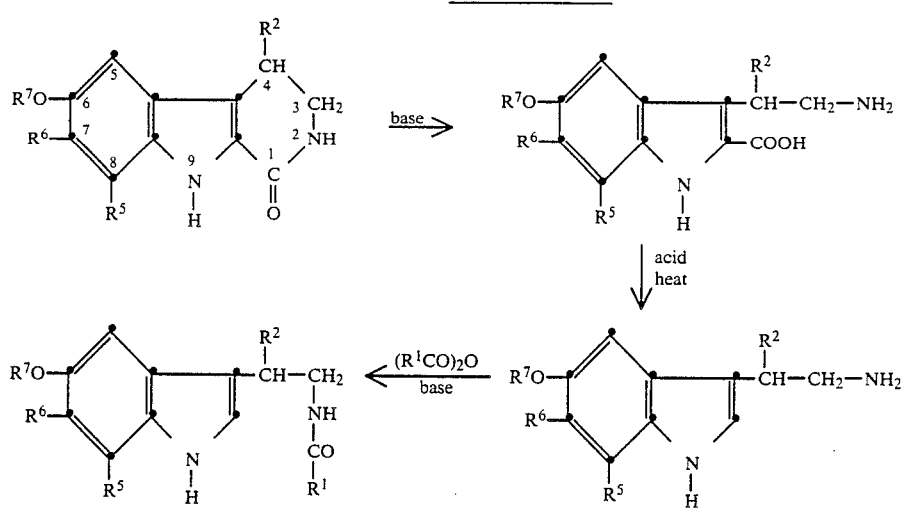

wherein all $R^1$, $R^2$, $R^5$, $R^6$, and $R^7$ have their previous meaning.

In the above procedure, a 5-alkoxy indole, permissibly mono or dihalogenated at C-6 and/or C-7 is reacted with a $C_1$–$C_4$ alkylaldehyde ($R^2$CHO) and Meldrum's acid (2,2-dimethyl-4,6-dioxo-1,3-dioxane) in the presence of proline to yield adduct I. The adduct is decomposed by reaction with copper powder and pyridine in a lower alcohol to yield the corresponding ester of a β-alkyl indole propionic acid.

The ester can be reacted with hydrazine to provide the hydrazide, which is converted to an azide with nitrous acid. The azide is decomposed under Curtius conditions to yield a lactam (1-oxo-4-alkyl 6-alkoxy-7,8-permissibly mono or di-halogenated-9H-1,2,3,4-tetrahydropyrido[3,4-b]indole). The lactam ring is opened by reaction with a base to yield the amino acid, a 2-alkyl-2-(2-carboxy-3-indolyl)ethylamine. Decarboxylation of the latter yields the 2-alkyl-2-(3-indolyl)ethylamine, acylation of which with a lower alkyl anhydride, acid chloride, or chloroformate in the presence of base (conveniently pyridine) yields a β-alkylmelatonin of the invention.

An alternative process for preparing the β-alkyl melatonins of this invention, particularly useful for preparing the 6 and/or 7-halo derivatives, involves cyclization of a phenyl hydrazone derivative according to the following scheme.

Reaction Scheme II

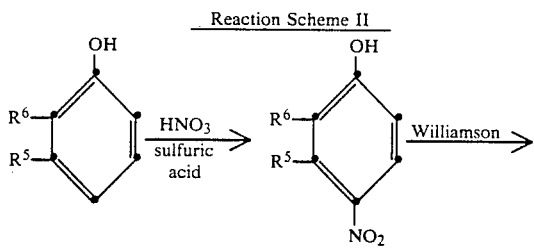

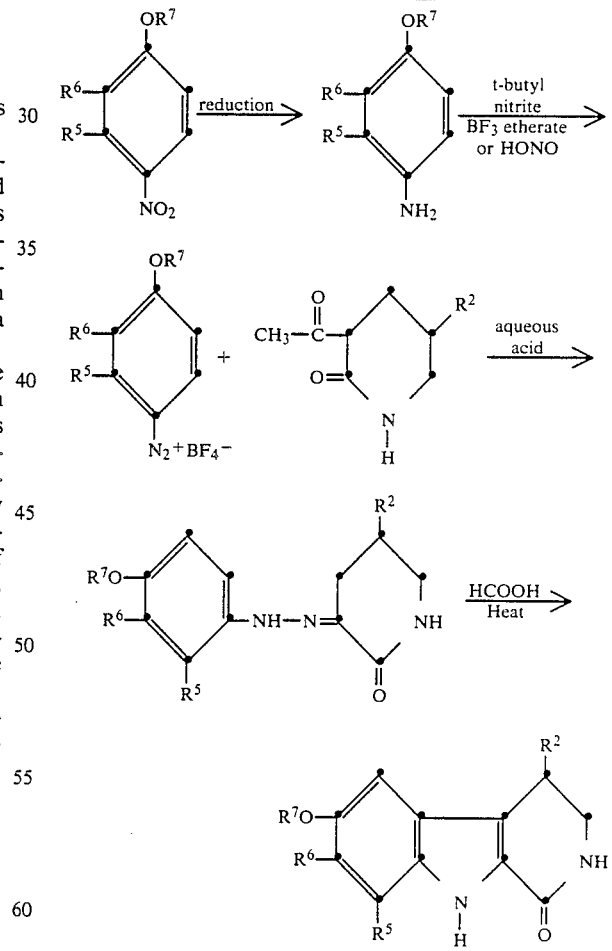

wherein $R^2$, $R^5$, $R^6$, and $R^7$ have their previous meaning.

In the above procedure, a phenol is nitrated para to the hydroxy group to yield a 4-nitrophenol. The 4-nitrophenol is methylated to yield a 4-nitro alkoxybenzene, reduction of which yields the 4-amino derivative.

A diazonium fluoroborate salt, prepared from the amine by standard procedures, is reacted with 3-acetyl-2-piperidone to yield a phenyl hydrazone. Heating the hydrazone with formic acid yields a 1-oxo-6-methoxy-1,2,3,4-tetrahydro-9H-pyrido[3,4-b]indole. The indole is reacted to the final product melatonin by the same sequence of reactions disclosed in Reaction Scheme I.

It will be noted that the above synthetic method yields halogenated melatonins of unambiguous structure since the preparation of the diazonium salt does not result in the production of mixtures. In addition, the intermediate used to react with the diazonium salt, a 5-alkyl-3-acetyl-2-piperidone, is a known compound which can be prepared by procedures previously disclosed in Ploner et al. *Chem Ber,* 100, 1675 (1967).

This invention also provides compounds where various substituents are attached to the 1-position nitrogen atom. Compounds of this invention in which $R^4$ is not hydrogen are prepared from the β-alkyl melatonin final products of Reaction Scheme I. They are prepared by treating the latter with an appropriate acylating agent. Typically, the side-chain N-acylated compound is reacted with at least an equimolar amount of an acyl halide of the formula $R^4Cl$, in which $R^4$ represents any of the groups defined above other than hydrogen. The reaction is carried out in the presence of a moderate molar excess (about 10%) of a strong base, such as sodium hydride, at room temperature in an inert solvent and for a time sufficient to accomplish conversion.

The β-alkyl melatonins of this invention have an asymmetric center, namely, the carbon atom carrying the alkyl group beta to the amide nitrogen atom. Thus the compounds of this invention exist as two enantiomorphs forming a racemate. This invention includes all such racemates and enantiomers.

The individual stereoisomers constituting the racemates can be prepared in optically active form by resolving the racemic 2-alkyl-2-(3-indolyl)ethylamine. This resolution can be accomplished by amide formation with an optically active acid, separation of the two diastereoisomeric forms, and hydrolysis of the amide group to yield separated d and l primary amines, which can each be converted to a melatonin or a melatonin analogue by reaction with $(R^1CO)_2O$ or an equivalent acylating agent. The preferred resolving agent is Mosher's acid, α-trifluoromethyl α-methoxy phenylacetic acid.

Alternatively, an optically active diterpene such as L-menthol or pulegone can be used to prepare enantiomorphs of β-methylmelatonins (R'is methyl). In this method L-menthol or pulegone is converted, according to Reaction Scheme III below, to an optically active 5-methyl-3-ethoxycarbonyl-2-piperidone which is reacted in a similar manner as the 5-alkyl-3-acetyl-2-piperidone compound of Reaction Scheme II to form the same (but optically active) phenyl hydrazone intermediate.

Reaction Scheme III

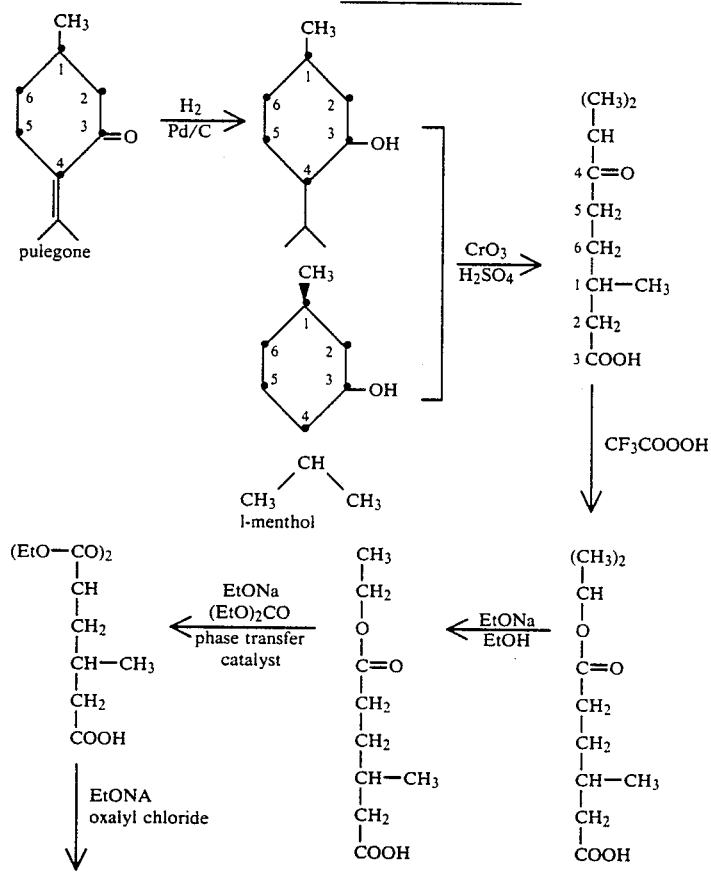

-continued

Reaction Scheme III

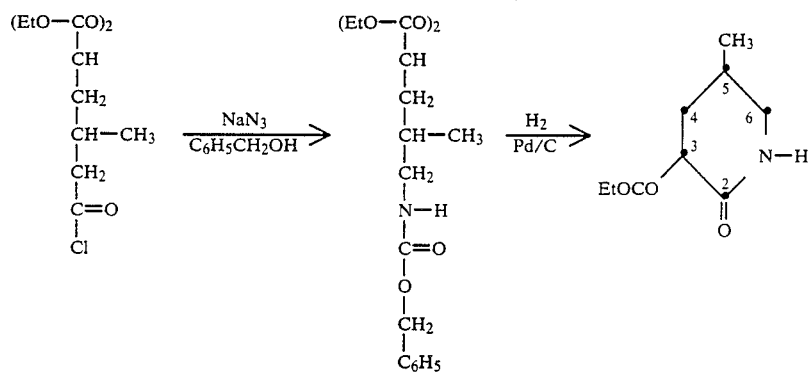

This invention is further illustrated by the following specific examples which are not intended to be limiting on the scope thereof.

EXAMPLE 1

Preparation of β-Methylmelatonin

To a cold (15° C.) solution of 17.9 g (0.12 mole) of 5-methoxyindole, 17.5 g (0.12 mole) of Meldrum's acid, and 5.34 g (0.12 mole) of acetaldehyde in 120 ml of acetonitrile were added 0.11 g of l-proline. The reaction mixture was cooled to prevent the temperature of the initially exothermic reaction from exceeding 25° C. The mixture was stirred at room temperature for five hours. The acetonitrile was removed under vacuum and the pale yellow oil that remained crystallized when chilled overnight at about 0° C. The crystalline product was washed with pet. ether and dried. The yield of adduct, m.p. 99°, was quantitative.

Analysis calc. for $C_{17}H_{19}NO_5$:
Theory: C, 64.34; H, 6.04; N, 4.41.
Found : C, 64.21; H, 6.14; N, 4.22.

A stream of nitrogen was passed through a mixture of 39 ml of ethanol and 110 ml of pyridine for several minutes to remove dissolved air. To this mixture was added 38.5 g (0.12 mole) of the above adduct followed by 0.76 g of copper dust. The mixture was refluxed under nitrogen for 16 hours. After cooling, the mixture was filtered through "Hyflo Super Cel". The solvents were immediately evaporated from the filtrate. The residual oil was dissolved in diethyl ether and the ethereal solution was washed with 1N HCl followed by a wash with 20% aqueous ammonium chloride. The organic layer was dried over anhydrous $Na_2SO_4$. The crude product obtained upon evaporation of the diethyl ether was chromatographed over silica gel using 3% MeOH in $CHCl_3$. The purified product, 23.3 g of an amber oil, was identified as 3-(5-methoxy-1H-indol-3-yl)pentanoic acid ethyl ester (74% yield).

Analysis calc. for $C_{15}H_{19}NO_3$:
Theory: C, 68.94; H, 7.33; N, 5.36.
Found: C, 69.18; H, 7.36; N, 5.27.

A mixture of 22.3 g (0.086 mole) of the above ester and 16.6 ml of hydrazine hydrate was refluxed under nitrogen. After 3½ hours, excess hydrazine hydrate was removed under vacuum. 2-Methyl-2-(5-methoxy-3-indolyl)propionhydrazide crystallized on standing. The filter cake was washed with ether; yield=16.5 g (78% yield) of colorless hydrazide. A sample melted at 117° C. after recrystallization from ethyl acetate.

Analysis calc. for $C_{13}H_{17}N_3O_2$:
Theory: C, 63.14; H, 6.93; N, 16.99.
Found: C, 62.96; H, 6.66; N, 17.15.

A mixture of 16.5 g (0.067 mole) of the above hydrazide, 100 ml of acetic acid, 200 ml of water and 200 g of ice was swirled while a solution of 6.21 g (0.09 mole) of sodium nitrite in 11 ml of water was gradually added. The resulting acyl azide was immediately extracted into cold diethyl ether. The extract was kept cold as it was washed with aqueous $NaHCO_3$ followed by a brine wash. The solution was dried over $Na_2SO_4$. The ether was evaporated in vacuo. The residual acyl azide was taken up in 200 ml of cold toluene. This solution was then added slowly to an additional 200 ml of toluene which was being mechanically stirred under nitrogen in an oil bath at 83° C. After the toluene addition stirring was continued for 15 minutes. The reaction mixture was allowed to cool to about 50°. A stream of dry HCl gas was passed into the solution for a few seconds. The mixture was then concentrated to one-half its volume and the resulting insoluble product was collected by filtration. The filter cake was washed with diethyl ether and dried to provide 5.79 g (38% yield) of 1-oxo-4-methyl-6-methoxy-1,2,3,4-tetrahydro-9H-pyrido[3,4-b]indole; m.p. 220° C.

Analysis calc. for $C_{13}H_{14}N_2O_2$:
Theory: C, 67.81; H, 6.13; N, 12.17.
Found: C, 67.54; H, 5.97; N, 12.37.

A suspension of 5.79 g (0.025 mole) of the above tetrahydropyridoindole in a solution consisting of 85 ml of ethanol, 60 ml of water, and 8.5 g of KOH was refluxed under nitrogen for 24 hours. After cooling, the ethanol was evaporated under vacuum. The remaining aqueous solution was chilled to about 0° C. as the solution pH was lowered to 6.0 using 1N hydrochloric acid. The precipitated amino acid was collected and dried under vacuum, without heat. The yield of crude product 5-methoxy-3-(1-amino-2-propyl)indole-2-carboxylic acid was essentially quantitative.

The above crude amino acid was immediately decarboxylated by refluxing in 150 ml of 5M methane-sulfonic acid under nitrogen for 47 minutes. After cooling, the solution was made basic by the addition of 5M aqueous NaOH. The decarboxylated product was extracted into ether. The ether extracts were dried over $Na_2SO_4$. Evaporation of the ether gave 3.92 g of crude tryptamine as a gummy solid. Washing the crude material with a small amount of cold toluene gave 2.48 g of crystalline product (48% yield) comprising purified 5-methoxy-3-(1-amino-2-propyl)indole.

A solution of 2.48 g (0.012 mole) of the above tryptamine in 18 ml of toluene and 4.5 ml of pyridine was treated with 2.5 ml of acetic anhydride. The mixture was stirred for four hours. The solvents were removed under vacuum. The resulting residue was taken up in $CH_2Cl_2$ and the mixture stirred for several hours with aqueous $NaHCO_3$ in order to decompose residual acetic anhydride. The $CH_2Cl_2$ solution was then dried over $Na_2SO_4$ and the solvent evaporated. Chromatography of the crude product over silica gel using ethyl acetate as eluent afforded 2.54 g (85% yield) of pure β-methylmelatonin as a colorless glass.

Analysis calc. for $C_{14}H_{18}N_2O_2$:
Theory: C, 68.27; H, 7.37; N, 11.37.
Found: C, 68.07; H, 7.50; N, 11.17.

EXAMPLE 2

Preparation of β-Ethylmelatonin

Following the procedure of Example 1, 5-methoxyindole, propionaldehyde, and Meldrum's acid were condensed. Because the reaction was somewhat more sluggish, a 50% excess of propionaldehyde was used and the reaction was allowed to proceed overnight. The yield of adduct, a pale yellow semi-solid, was quantitative.

Analysis calc. for $C_{18}H_{21}NO_5$:
Theory: C, 65.24; H, 6.59; N, 4.23.
Found: C, 65.46; H, 6.58; N, 3.99.

Following the procedure of Example 1, the adduct was solvolyzed with ethanol in the presence of pyridine and copper dust. Decarboxylation was somewhat less facile than in the previous case. Thus, after the mixture had been refluxed for 19 hours, it was necessary to complete the reaction by boiling off the excess ethanol and then refluxing at 115° C. for another 6½ hours. The yield of ester —3-(5-methoxy-1H-indol-3-yl)pentanoic acid ethyl ester—after silica gel chromatography, using 2% EtOAc in toluene as the eluant, was 60%.

Analysis calc. for $C_{16}H_{21}NO_3$:
Theory: C, 69.79; H, 7.69; N, 5.09.
Found: C, 69.53; H, 7.40; N, 5.01.

The above-prepared ester was refluxed in hydrazine hydrate as previously described. Complete reaction required 6½ hours. The yield of 2-ethyl-2-(5-methoxy-3-indolyl)propionhydrazide, after recrystalization from ethyl acetate, was 45%; m.p. 101°–103° C.

Analysis calc. for $C_{14}H_{19}N_3O_2$:
Theory: C, 64.35; H, 7.33; N, 16.08.
Found: C, 64.20; H, 7.53; N, 15.88.

The corresponding hydrazide was converted to acyl azide, and the azide thermally rearranged, and cyclized, to the lactam 1-oxo-4-ethyl-6-methoxy-1,2,3,4-tetrahydro-9H-pyrido[3,4-b]indole according to the procedure of Example 1. Instead of allowing the final product to crystallize from the concentrated reaction mixture, the toluene was completely evaporated affording a residue comprising crude lactam; yield=75%. A sample of the lactam was recrystallized from acetone/water for analysis.

Analysis calc. for $C_{14}H_{16}N_2O_2$:
Theory: C, 68.83; H, 6.60; N, 11.47.
Found: C, 68.68; H, 6.74; N, 11.37.

Hydrolysis of the lactam was carried out as previously described in Example 1. The yield of crude 2-carboxy-3-(1-amino-2-butyl)-5-methoxyindole was 96%. As before, it was decarboxylated without further purification (the only change from the procedure in Example 1 being that 3M methanesulfonic acid was employed). Several hours were required for complete reaction. The yield of the tryptamine, 3-(1-amino-2-butyl)-5-methoxyindole, was 36%. The crude product, an oil, was acetylated directly without further purification in the manner described in Example 1 for the β-methyl compound. The product, β-ethyl melatonin thus prepared, after silica gel chromatography, was a colorless glass.

Analysis calc. for $C_{15}H_{20}N_2O_2$:
Theory: C, 69.20; H, 7.74; N, 10.76.
Found: C, 69.25; H, 7.99; N, 10.59.

EXAMPLE 3

Preparation of β-Methyl-6-chloromelatonin

Following the procedure of Example 1, a solution of 10.0 g (0.055 mole) of 5-methoxy-6-chloroindole, 3.1 ml (2.44 g, 0.055 mole) of acetaldehyde, and 7.94 g (0.055 mole) of Meldrum's acid in 90 ml of acetonitrile was stirred for 48 hours. The solvent was removed under vacuum, and the adduct thus prepared was recrystallized by dissolving in warm toluene and immediately cooling. The adduct was obtained as slightly pink crystals; m.p.=145° C.; yield=16.5 g (85%). The elemental analysis of the product showed a slightly elevated percentage of carbon. However, the NMR spectrum indicated that the product was pure and had the indicated structure.

Analysis calc. for $C_{17}H_{18}NO_5Cl$:
Theory: C, 58.04; H, 5.16; N, 3.98; Cl, 10.08.
Found: C, 59.34; H, 5.15; N, 3.84; Cl 9.69.

The solvolysis and decarboxylation of the adduct (11.0 g; 31.3 mmoles) using ethanol, pyridine, and copper dust was carried out by the procedure of Example 1. The yield of 3-(5-methoxy-6-chloro-1H-indol-3-yl)pentanoic acid ethyl ester, a pale yellow oil, after chromatography over silica gel using 10% EtOAc/90% toluene was 8.68 g (94%).

Analysis calc. for $C_{15}H_{18}NO_3Cl$:
Theory: C, 60.91; H, 6.13; N 4.74; Cl 11.99.
Found: C, 60.67; H, 5.86; N, 4.93; Cl, 11.73.

A mixture of 8.68 g (29.3 mmoles) of the above ethyl ester and 6 ml of hydrazine hydrate was heated at 140° C. under nitrogen in a flask fitted with an air cooled condensor. After 6½ hours, the excess hydrazine hydrate was removed under vacuum. The 2-methyl-2-(5-methoxy-6-chloro-3-indolyl)-propionhydrazide thus prepared was recrystallized from ethyl acetate; Yield=7.13 g (86%); m.p.=154°–155° C.

Analysis calc. for $C_{13}H_{16}N_3O_2Cl$:
Theory: C, 55.42; H, 5.72; N, 14.91; Cl, 12.58.
Found: C, 55.14; H, 5.51; N, 14.49; Cl, 12.78.

The above hydrazide (7.13 g, 25 mmoles) was converted to the corresponding acyl azide, the azide thermolyzed and rearranged at 80° in toluene, and the rearranged product cyclized with HCl according to the procedure of Example 1. The yield of crude, light tan, lactam, 1-oxo-4-methyl-6-methoxy-7-chloro-1,2,3,4-tetrahydro-9H-pyrido[3,4-b]indole, product (m.p. =249°-252° C.) was 4.77 g (72%).

Analysis calc. for $C_{13}H_{13}N_2O_2Cl$:
Theory: C, 58.99; H, 4.95; N, 10.58.
Found: C, 59.45; H, 4.77; N, 10.72.

The crude lactam (4.77 g, 18 mmoles) was hydrolyzed with aqueous ethanolic KOH as described in Example 1. The yield of crude amino acid, 2-carboxy-3-(1-amino-2-propyl)-5-methoxy-6-chloroindole, was 3.98 g (78%). The crude product (3.0 g; 10.6 mmoles) was decarboxylated, using the procedure of Example 1, by refluxing in 100 ml of 3M HCl overnight. The acidic solution was decolorized with activated carbon and was then basified with 5M NaOH. The amine was extracted into diethyl ether. After drying the ether extract over Na$_2$SO$_4$, the diethyl ether was removed in vacuo leaving as a residue the crystallized tryptamine, 3-(1-amino-2-propyl)-5-methoxy-6-chloroindole; m.p. 133°–4° C. The yield, after recrystallization from toluene/hexane, was 1.62 g (64%).

Analysis calc. for C$_{12}$H$_{15}$N$_2$OCl:
Theory: C, 60.38; H, 6.33; N, 11.74; Cl, 14.85.
Found: C, 60.11; H, 6.05; N, 11.93; Cl, 15.06.

A solution of 1.51 g (6.3 mmoles) of the above tryptamine in 10 ml of toluene and 2.5 ml of pyridine was treated with 1.5 ml of acetic anhydride. After allowing the reaction mixture to stand for three hours at room temperature, the volatile materials were removed under vacuum. The residue was dissolved in ethyl acetate, and washed with aqueous NaHCO$_3$, and brine. The ethyl acetate solution was dried over Na$_2$SO$_4$, and the solvent removed by evaporation. The residual oil was crystallized from toluene/hexane yielding 6-chloro-β-methyl-melatonin, (m.p.=133°–5° C.; 1.09 g, 61%).

Analysis calc. for C$_{14}$H$_{17}$N$_2$O$_2$Cl:
Theory: C, 59.89; H, 6.10; N, 9.98; Cl, 12.63:
Found: C, 60.03; H, 6.22; N, 9.75; Cl, 12.92.

EXAMPLE 4

Preparation of β-methyl-6,7-dichloromelatonin

To a chilled solution (below 0° C.) of 13.2 ml of freshly distilled boron trifluoride etherate in 125 ml of methylene chloride, in a 1 liter 3-neck round bottom flask equipped with nitrogen inlet tube and stirrer, were added 13.7 g of 4-amino-2,3-dichloroanisole and 65 ml of methylene chloride. The addition was made over a 20 minute period with vigorous stirring. Next, a solution of 10.6 ml of t-butyl nitrite and 65 ml of methylene chloride was added dropwise over a 30 minute period to the reaction mixture. After the addition had been completed the reaction mixture was kept below about 0° C., with stirring, for about 40 minutes. Then 375 ml of pentane were added to desolubilize the 2,3-dichloro-4-methoxybenzenediazonium fluoroborate formed in the above reaction. The diluted reaction mixture was stirred for an additional hour, then filtered. The filter cake, comprising the diazonium salt, was dried in vacuo to yield a white powder melting at 153°–154° C. with decomposition.

To a solution of 2.81 g (9.67 mmoles) of 2,3-dichloro-4-methoxybenzenediazonium fluoroborate in 38 ml of water and 46 ml of acetic acid were added 1.50 g (9.67 mmoles) of 3-acetyl-5-methyl-2-piperidone. Within about 1 minute 3-[2-(2,3-dichloro-4-methoxy)phenyl hydrazono]-5-methyl-2-piperidone commenced to separate. After stirring for 20 minutes 21 ml of water were added. Stirring was continued for another hour. The reaction mixture was then chilled for several hours and 3-(substituted phenylhydrazono)-5-methyl-2-piperidone was collected by filtration; m.p. 211°–214° C.; Yield=2.87 g (94%).

Analysis calc. for C$_{13}$H$_{15}$N$_3$O$_2$Cl$_2$:
Theory: C, 49.38; H, 4.78: N, 13.29.
Found: C, 49.56; H, 4.90; N, 13.20.

A mixture of 2.87 g (9.08 mmoles) of the hydrazonopiperidone and 90 ml of 85% formic acid was heated at about 100° C. for one hour. The hot solution was diluted slowly with 18 ml of water at which point the 1-oxo-4-methyl-6-methoxy-7,8-dichloro-1,2,3,4-tetrahydro-9H-pyrido[3,4-b]indole formed in the reaction commenced to separate. After chilling the reaction mixture for several hours the product was collected by filtration and recrystallized from ethanol. The yield of colorless, crystalline product was 1.85 g (68%).

Analysis calc. for C$_{13}$H$_{12}$N$_2$O$_2$Cl$_2$:
Theory: C, 52.19; H, 4.04; N, 9.36.
Found: C, 52.32; H, 4.15; N, 9.19.

Following the procedure of Example 2, 1.85 g (6.18 mmoles) of 1-oxo-4-methyl-6-methoxy-7,8-dichloro-1,2,3,4-tetrahydro-9H-pyrido[3,4-b]indole were hydrolyzed with aqueous alcoholic KOH. The yield of crude amino acid, 2-carboxy-3-(1-amino-2-propyl)-5-methoxy-6,7-dichloroindole, thus formed was quantitative. The amino acid was decarboxylated without further purification, using the procedure of Example 2, with 3M hydrochloric acid for 48 hours to yield 3-(1-amino-2-propyl)-5-methoxy-6,7-dichloroindole.

The hydrolysis solution was cooled, then made basic by the addition of 1N NaOH. After chilling the solution the product was collected by filtration, then dried. The filter cake was washed with cold CH$_2$Cl$_2$. The 3-(1-amino-2-propyl)-5-methoxy-6,7-dichloroindole thus prepared was a slightly tan solid weighing 1.05 g (62% yield).

Analysis calc C$_{12}$H$_{14}$N$_2$OCl$_2$:
Theory: C, 52.76; H, 5.17; N, 10.26.
Found: C, 52.52; H, 5.36; N, 9.97.

The acetylation of 1.05 g (3.84 mmoles) of the tryptamine with acetic anhydride was carried out as described in Example 2. The β-methyl-6,7-dichloro melatonin thus prepared was purified by digesting in ether. The yield of colorless product was 0.80 g (66%)

Analysis calc. for C$_{14}$H$_{16}$N$_2$O$_2$Cl$_2$:
Theory: C, 53.35; H, 5.12; N, 8.89; Cl, 22.50.
Found: C, 53.09; H, 5.15; N, 9.06; Cl, 22.51.

EXAMPLE 5

Preparation of R-(−) and S-(+) 3-ethoxy-carbonyl-5-methyl-2-piperidone.

A mixture of 156 g (1 mole) of (L)-menthol and 1032 g of 35% sulfuric acid was stirred mechanically while a solution of 220 g (2.2 moles) of chromium trioxide in 1032 g of 35% sulfuric acid was added at a rate such that the reaction temperature did not exceed 30° C. Stirring was continued at 30° C. for 3½ hours. The reaction mixture was extracted repeatedly with diethyl ether. The ether extracts were combined, concentrated, and then extracted with 1M aqueous NaOH. The aqueous extract was acidified with 12N hydrochloric acid and then extracted several times with diethyl ether. The ether extracts were combined, washed with brine and dried over Na$_2$SO$_4$. After evaporating the diethyl ether, the residue, comprising S-(+)-3,7-dimethyl-6-oxooctanoic acid formed by the above oxidation, was distilled. The yield of redistilled ketoacid, bp (0.05 mm Hg)=104° C., was 74 g (40%). [α]$^{25}$=+7.8° (c=10, MeOH).

Analysis calc. for C$_{10}$H$_{18}$O$_3$:
Theory: C, 64.49; H, 9.74.
Found: C, 64.41; H, 9.48.

A solution of peroxytrifluoroacetic acid, prepared by slow addition of 16.4 ml (0.60 mole) of 90% hydrogen peroxide to a mixture of 100 ml (149 g, 0.71 mole) of trifluoroacetic anhydride and 100 ml of methylene chloride, was slowly added to a mixture of 74 g (0.40 mole) of S-(+)-3,7-dimethyl-6-oxooctanoic acid, 400 ml of methylene chloride, and 102 g (0.72 mole) of disodium hydrogen phosphate. This reaction mixture was stirred for 48 hours at room temperature (24° C.) and then washed thoroughly, first with water, then brine. After drying over Na$_2$SO$_4$ the solvent was evaporated and the residual liquid was distilled affording 64.2 g (79% yield) of S-(+)-3-methyl-5-isopropoxycarbonylpentanoic acid, bp (0.05 mm Hg)=101°-107° C. [α]$^{25}$=+6.4° (c=10, MeOH).

Analysis calc. for C$_{10}$H$_{18}$O$_4$:
Theory: C, 59.39; H, 8.97.
Found: C, 59.23; H, 8.69.

A solution of 50 g (0.25 mole) of the above isopropyl ester in 250 ml of anhydrous 2M ethanolic sodium ethoxide was stirred at 40° C. for three hours. The cooled solution was poured into a mixture of ice and excess 2M hydrochloric acid then extracted with diethyl ether. The ether extract was washed with brine, then dried. The ether was evaporated and the liquid residue distilled. The yield of S-(+)-3-methyl-5-ethoxycarbonyl pentanoic acid, bp (0.03 mm Hg)=100° C., was 33.2 g (71%). [α]$^{25}$=+6.6° (c=10, MeOH).

Analysis calc. for C$_9$H$_{16}$O$_4$:
Theory: C, 57.43; H, 6.57.
Found: C, 57.46; H, 8.28.

Sodium ethoxide was prepared in a 500 ml, three-necked, flask by dissolving 13.1 g (0.57 g-atoms) of sodium in 100 ml of absolute ethanol. Most of the excess ethanol was removed under vacuum. Then 260 ml of ethyl carbonate and 9.0 g of "Adogen 464" (a phase transfer catalyst) were added. The flask was fitted with a mechanical stirrer, a 250 ml dropping funnel (without pressure equalizing side arm), and a jacketed 21 cm Widmer column. Heating the flask in an oil bath at 160° C. caused the balance of the ethanol to distill off and brought the ethyl carbonate to the point where it distilled very slowly through the Widmer column. While heating at 160° C. 26.8 g (0.14 mole) of S-(+)-3-methyl-5-ethoxycarbonylpentanoic acid in 100 ml of ethyl carbonate were added over a one hour period. After an additional hour of heating, ethanol distillation had ceased, and the temperature of the distilling ethyl carbonate had reached 125°-6° C. The mixture was cooled and the sodium salt of S-(+)-3-methyl-5-bis(ethoxycarbonyl)pentanoic acid was collected and quickly washed with a small amount of THF. The salt was then added to a mixture of ice and excess 2M HCl, then extracted into diethyl ether. The ether extract was washed with brine and dried over Na$_2$SO$_4$. The diethyl ether was evaporated and the residue subjected to HPLC chromatography over a Waters "Prep 500" silica gel column using methylene chloride followed by 1% methanol in methylene chloride as the eluant. Fractions containing S-(+)-3-methyl-5bis(ethoxycarbonyl)pentanoic acid as determined by TLC were pooled and the solvent recovered from the pooled fractions to yield S-(+)-3-methyl-5-bis(ethoxycarbonyl)pentanoic acid.

A solution of 4.31 g (16.6 mmoles) of S-(+)-3-methyl-5-bis(ethoxycarbonyl)pentanoic acid in 50 ml of ethanol was treated with one equivalent of ethanolic sodium ethoxide. The ethanol was removed in vacuo and the residual salt thoroughly dried. This salt was suspended in cold benzene and treated with 1.44 ml (2.10 g, 16.5 mmoles) of oxalyl chloride. After the initial rapid reaction ceased, the solution was filtered and the benzene evaporated under vacuum. The acid chloride formed was solubilized in a small amount of acetone and added to a solution of 1.19 g (17 mmoles) of sodium azide in 6 ml of water at a rate such that the temperature was maintained at 10°-15° C. After one hour, S-(+)-3-methyl-5-bis(ethoxycarbonyl)pentanoyl azide was extracted into benzene. The extract was dried over Na$_2$SO$_4$, and the solvent removed under vacuum. The residue was placed in solution with a small amount of dioxane (~0.5 ml) and added dropwise to 5 ml of benzyl alcohol which had been heated to 140° C. After heating for an additional 30 minutes the excess benzyl alcohol was removed under vacuum, leaving 2.9 g (48% yield) of benzyl N-S-(+)-[2-methyl-4-bis(ethoxycarbonyl)]butyl-carbamate. A small sample of this material was further purified by silica gel chromatography. [α]$^{25}$=+9° (c=10, MeOH).

Analysis calc. for C$_{19}$H$_{27}$NO$_6$:
Theory: C, 62.45; H, 7.45; N, 3.83.
Found: C, 62.26; H, 7.51; N, 3.72.

A solution of the above carbamate (2.7 g, 7.4 mmoles) in 200 ml of ethanol was hydrogenated over 0.5 g of 10% Pd/C. When hydrogen uptake ceased the catalyst was removed by filtration and the filtrate allowed to stand at room temperature (24° C.) for 48 hours. After evaporating the solvent the residual lactam, S-(+)-3-ethoxycarbonyl-5-methyl-2-piperidone, was crystallized from diethyl ether, affording 1.10 g (80% yield) of crystalline material; m.p. 93°-94°. [α]$^{25}$=+36.7° (c=10, MeOH).

Analysis calc. for C$_9$H$_{15}$NO$_3$:
Theory: C, 58.35; H, 8.16; N, 7.56.
Found: C, 58.23; H, 7.68; N, 7.60.

R-(−)-3-ethoxycarbonyl-5-methyl-2-piperidone was prepared in similar fashion by reacting a mixture of 156 g (1 mole) of crude (−)-methone and (+)-isomenthone (obtained by hydrogenation of (+)-pulegone over Pd/C), suspended in 687 g of 35% sulfuric acid, with a solution of 146 g (1.46 moles) of chromium trioxide in 687 g of 35% sulfuric acid. The chromium trioxide solution was added at a rate such that the reaction temperature did not exceed 30° C. Stirring was continued for another 3½ hours after which the product, R-(−)-3,7-dimethyl-6-oxooctanoic acid, was extracted into diethyl ether. The ether extract was concentrated and extracted with 1M aqueous NaOH. The aqueous extract was acidified with 12N hydrochloric acid and then extracted with diethyl ether. The ether extract was washed with brine then dried over Na$_2$SO$_4$, and the ether removed under vacuum. The residue was distilled affording 74.7 g (40% yield) of R-(−)-3,7-dimethyl-6-oxooctanoic acid, bp (0.05 mm Hg)=110° C. This product was identical to that obtained by oxidation of (L)-menthol except that it exhibited the opposite sign of rotation.

Carrying the (R)-(−)ketoacid through all the steps described above for the (S)-(+) isomer afforded the (R)-(−)-3-ethoxYcarbonyl-5-methyl-2-piperidone. This isomer was identical to the (S)-(+)product in all respects except for the sign of the rotation of plane polarized light.

EXAMPLE 6

Preparation of S-(−)-β-Methylmelatonin and R-(+)-β-Methylmelatonin

Following the procedure of Example 4, a mixture of 2.50 g (13.5 mmoles) of (R)-(−)-3-ethoxycarbonyl-5-methyl-2-piperidone and 40 ml of 0.75M NaOH was stirred at room temperature (24° C.) for 20 hours, then chilled to 0° C. The pH was lowered to about 3.5 with 3M hydrochloric acid, and 3.00 g (13.5 mmoles) of p-anisyldiazonium tetrafluoroborate (prepared from p-anisole by the procedure set forth in Example 4) were added in small portions. The reaction mixture was chilled to about 0° C. overnight. The crude product was collected by filtration, washed with cold water, then dried. Yield of crude hydrazone, R-(−)-3-(p-methoxy-phenylhydrazono)-5-methyl-2-piperidone, m.p. 201° C., was 2.50 g (75% yield). A small sample of hydrazone was further purified by passage over a short silica gel column with ethyl acetate as the eluant; rotation $[\alpha]^{25} = -82°$ (c=9.5, MeOH).

Analysis calc. for $C_{13}H_{17}N_3O_2$:
Theory: C, 63.14; H, 6.92; N, 16.99.
Found: C, 62.97; H, 6.80; N, 16.88.

A mixture of 2.30 g (9.3 mmoles) of hydrazone and 17 ml of 85% formic acid was heated at 85°–90° C. for three hours. Water was then added dropwise until crystallization commenced. The crystallization mixture was cooled, then chilled overnight. The crude product was collected by filtration, washed with water, then dried. Yield of crude S-(−)-lactam, S-(−) 1-oxo-4-methyl-6-methoxy-1,2,3,4-tetrahydro-9H-pyrido[3,4]-indole, (m.p. 215° C.) was 1.41 g (66%). A small sample was recrystallized from an acetone/water solvent mixture. This product was spectroscopically identical to the racemic material previously described in Example 1; rotation $[\alpha]^{25} = -6°$ (c=5, MeOH).

Analysis calc. for $C_{13}H_{14}N_2O_2$:
Theory: C, 67.81; H, 6.13; N, 12.17.
Found: C, 67.51; H, 5.99; N, 11.94.

The conversion of the (S)-(−)-lactam to the (S)-(−)-β-methylmelatonin was carried out as described in Example 1 for the preparation of the racemate. The final product S-(−)-β-methylmelatonin was spectroscopically identical to that of the racemate; rotation $[\alpha]^{25} = -5.6°$ (c=5, MeOH).

(R)-(+)-β-methylmelatonin was synthesized from (S)-(+)-3-ethoxycarbonyl-5-methyl-2-piperidone as described above. It was spectroscopically identical to the above (S)-(−) material but exhibited the opposite sign of rotation.

EXAMPLE 7

Preparation of S-(−)-β-methyl-6-chloromelatonin and R-(+)-β-methyl-6-chloromelatonin A solution of 4.0 g (21 mmoles) of 3-chloro-4-methoxynitrobenzene in 200 ml of toluene was hydrogenated over 0.4 g of 5% platinum on alumina. The catalyst was removed by filtration and the solvent evaporated from the filtrate. The crude 3-chloroanisidine prepared was placed in solution in diethyl ether and treated with ethereal HCl to produce the hydrochloride salt, which was collected and dried; weight=2.48 g (61% yield).

A mixture of 2.40 g (12.4 mmoles) of 3-chloroanisidine hydrochloride in 7 ml of 4M HCl was treated, at 0° C., with 0.86 g (12.5 mmoles) of sodium nitrite in 5 ml of water. After stirring at 0° C. for an hour the solution was filtered and the filtrate added slowly to an ice cold solution of 2.6 g (24 mmoles) of sodium fluoroborate in 8 ml of water. After stirring at 0° C. for an hour the salt was collected and washed successively with, cold 5% sodium fluoroborate solution, cold methanol, and ether. The dried 3-chloro-4-methoxybenzene diazonium fluoroborate thus prepared weighed 2.2 g (69% yield).

A mixture of 2.03 g (11.0 mmole) of (R)-(−)-3-ethoxycarbonyl-5-methyl-2-piperidone and 30 ml of 0.75M NaOH was stirred at room temperature (24° C.) overnight. The solution was cooled to 0° C. and the pH lowered to 3.5 with 3M hydrochloric acid. The diazonium salt (2.8 g, 10.9 mmoles) was added in small portions and the reaction mixture cooled to about 0° C. overnight. The product, R-(−)-3-(3-chloro-4-methoxy-y)phenylhydrazono-5-methyl-2-piperidone, was collected, washed with water, and dried; weight=2.30 g (75% yield); m.p.=205° C. A small sample was further purified by chromatography over a short silica gel column using ethyl acetate as the eluant. $[\alpha]^{25} = -58°$ (c=10, MeOH).

Analysis calc. for $C_{13}H_{16}N_3O_2Cl$:
Theory: C, 55.42; H, 5.72; N, 14.91; Cl, 12.58.
Found: C, 55.79; H, 5.78; N, 14.72; Cl, 12.69.

A mixture of 2.20 g (7.8 moles) of the R-(−) hydrazone and 20 ml of 90% formic acid was heated at 85° for three hours then slowly diluted with an equal volume of water. The mixture was allowed to cool and then chilled overnight. The dark precipitate was collected, washed with water, then recrystallized from acetone/water, yielding 1.20 g (60% yield) of S-(−)-1-oxo-4-methyl-6-methoxy-7-chloro-1,2,3,4-tetrahydro-9H-pyrido[3,4-b]-indole; m.p.=248° C. $[\alpha]^{25} = -12.2°$ (c=10, MeOH).

Analysis calc. for $C_{13}H_{13}N_2O_2Cl$:
Theory: C, 58.99; H, 4.95; N, 10.58; Cl, 13.39.
Found: C, 59.16; H, 4.88; N, 10.80; Cl, 13.15.

The conversion of (S)-(−)-lactam to (S)-(−)-6-chloro-β-methylmelatonin was carried out as described previously in Example 3. The product, S-(−)-β-methyl-6-chloromelatonin, was spectroscopically identical to the racemate, but gave an optical rotation of $[\alpha]^{25} = -13.2°$ (c=10, MeOH).

(R)-(+)-6-chloro-β-methylmelatonin was synthesized from (S)-(+)-3-ethoxycarbonyl-5-methyl-2-piperidone in the same manner as described above. The stereoisomer was identical to the (S)-(−) material except for the sign of rotation.

The compounds of the invention are ovulation inhibitors. The degree of ovulation inhibitory activity was determined according to the following protocol.

Adult female rats with regular estrus cycles of four days each are employed. The estrus cycle consists of 2 days of diestrus followed by a day of proestrus and then a day of estrus. Daily vaginal smears were recorded, and rats were selected after they had demonstrated at least two consecutive 4-day estrus cycles. On the afternoon of proestrus, luteinizing hormone (LH) is released into the blood by the pituitary gland. The LH travels to the ovary where it induces ovulation, resulting in the presence of eggs in the oviduct on the day of estrus.

The test compound is administered orally to the non-control rats at noon on the day of proestrus. Both control and non-control rats are sacrificed on the following day (estrus). The oviduct is removed from each rat and examined microscopically for the presence of ova. A 50% decrease in the number of ovulating non-control rats, relative to the number of ovulating control rats, indicates the compound is active in blocking ovulation and establishes the minimum effective dose needed to inhibit ovulation.

Table I below discloses the results obtained when testing some β-methyl melatonins in the above procedure. Melatonin is included in Table I for comparative purposes. Column 1 gives the name of the compound, and column 2 the minimum effective inhibitory dose in mgs per kilogram of rat weight.

TABLE I

| Name of Compound | Minimum effective inhibitory dose in mg per kilogram of rat weight |
| --- | --- |
| Melatonin | 32.0 |
| β-methyl melatonin | 1.0 |
| R-(+)-β-methyl melatonin | 1.0* |
| β-ethyl melatonin | 1.0 |
| β-methyl-6-chloro-melatonin | 2.0 |
| R-(+)-β-methyl-6-chloromelatonin | 1.0 |
| S-(−)-β-methyl-6-chloromelatonin | >5.0 |
| β-Methyl-6,7-dichloro-melatonin | 15.0 |

*Blocked 40% of non-control rats relative to control rats at this dosage.

The β-alkyl derivatives also have a longer anovulatory effect than the α-methyl derivatives or the monohalo derivatives of the art. Thus they can be administered one or two hours prior to noon on the day of proestronus and still act as ovulation inhibitors.

As ovulation inhibitors, the compounds of this invention can be used as contraceptive agents in female mammals and birds. Their oral activity renders them particularly useful in achieving contraception, and population control, of unwanted (in their present numbers) mammalian species. For example, the compounds of this invention can be formulated in combination with baits and/or attractants and placed in feeding stations accessible to undesirable rodents and other small animals including Canidae such as coyotes, foxes, jackals, and wild dogs; and birds, such a starlings, gulls, redwing blackbirds, pigeons, and the like, to greatly reduce the excess population. They can also be used to reduce hazards to aviation by lessening the presence of birds and animals on runways in the vicinity of air fields. They also can be used to reduce the population of undesirable birds and animals so as to aid in the prevention and the spread of disease, and to reduce the destruction of property in both rural and urban areas.

The compounds of this invention can be administered as such, or they can be compounded and formulated into pharmaceutical preparations in unit dosage form for oral or parenteral administration. In the compounding or formulation, organic or inorganic solids and/or liquids which are pharmaceutically acceptable carriers or diluents can be employed. Suitable such carriers will be well recognized by those of ordinary skill in the art. The oral compositions may take the form of tablets, powder granules, capsules, suspensions, solutions, and the like.

The compounds of this invention, when administered in an effective amount will inhibit ovulation and therefore conception in birds and mammals. The usual daily dose is from about 0.02 milligrams to about 20 milligrams per kilogram body weight of the recipient. The preferred daily dose is from about 1 milligram to about 8 milligrams per kilogram body weight of the recipient.

I claim:

1. A compound of the formula

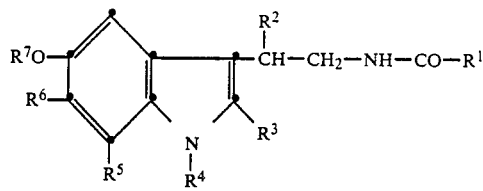

wherein
$R^1$ is H, $C_1$–$C_4$ alkyl, or $C_1$–$C_4$ alkoxy;
$R^2$ is $C_1$–$C_4$ alkyl;
$R^3$ is H;
$R^4$ is H, haloacetyl, $C_1$–$C_5$ alkanoyl, benzoyl, or benzoyl substituted with halo or methyl;
$R^5$ and $R^6$ are individually H or halo; and $R^7$ is H or $C_1$–$C_4$alkyl.

2. A compound of claim 1 wherein
$R^1$ is $C_1$–$C_4$ alkyl;
$R^2$ is $C_1$–$C_4$ alkyl;
$R^3$ and $R^4$ are H;
$R^5$ and $R^6$ are each individually H or halo; and $R^7$ is $C_1$–$C_4$ alkyl.

3. A compound of claim 2 wherein
$R^1$ is $C_1$–$C_4$ alkyl;
$R^2$ is methyl or ethyl;
$R^3$ and $R^4$ are H;
$R^5$ and $R^6$ are each individually H, F or Cl; and $R^7$ is methyl.

4. A compound according to claim 3, said compound being β-methyl 6,7-dichloromelatonin.

5. A compound according to claim 3, said compound being β-methyl melatonin.

6. A compound according to claim 3, said compound being β-methyl 6-chloromelatonin.

7. A pharmaceutical formulation comprising a compound of claim 1 together with a pharmaceutically acceptable carrier or diluent.

8. A method for inhibiting ovulation in a female mammal or bird comprising administering an anti-ovulent compound of claim 1 in doses from about 0.02 milligrams to about 20 milligrams per kilogram body weight of the recipient.

* * * * *